United States Patent [19]
Wheeler

[11] Patent Number: 5,916,223
[45] Date of Patent: Jun. 29, 1999

[54] TISSUE STAPLE REMOVER

[76] Inventor: Alton D. Wheeler, 3940 Fox Meadow La., Pasadena, Tex. 77504

[21] Appl. No.: 08/962,921

[22] Filed: Oct. 27, 1997

[51] Int. Cl.$^6$ .................................................... A61B 17/00
[52] U.S. Cl. ............................................................ 606/138
[58] Field of Search ...................... 606/219, 138, 606/220, 221, 151; 254/28; 29/268; 140/106; 72/409.01

[56] References Cited

U.S. PATENT DOCUMENTS

| | | | |
|---|---|---|---|
| 2,733,893 | 2/1956 | Segal | 254/28 |
| 2,741,457 | 4/1956 | Furumizo | 254/28 |
| 4,513,951 | 4/1985 | Rogers | 254/28 |
| 4,589,631 | 5/1986 | Markus | 254/28 |
| 5,451,231 | 9/1995 | Rabenau et al. | 606/138 |
| 5,653,424 | 8/1997 | Khan | 254/28 |

Primary Examiner—Michael Buiz
Assistant Examiner—Vikki Trinh
Attorney, Agent, or Firm—William W. Haeflinger

[57] ABSTRACT

In a surgical staple remover, the combination comprises multiple parts having operative interconnection, and relatively movable to retract a removed staple from a tissue zone; and a storage zone toward which removed staples are retracted for storage in response to relative movement of parts, a storage zone carried by at least one of the parts.

13 Claims, 5 Drawing Sheets

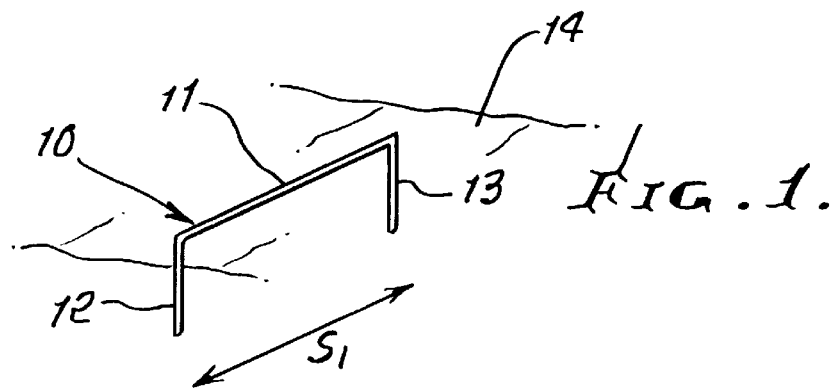
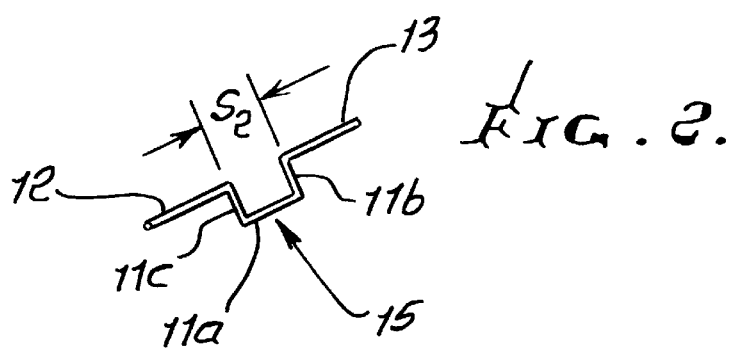
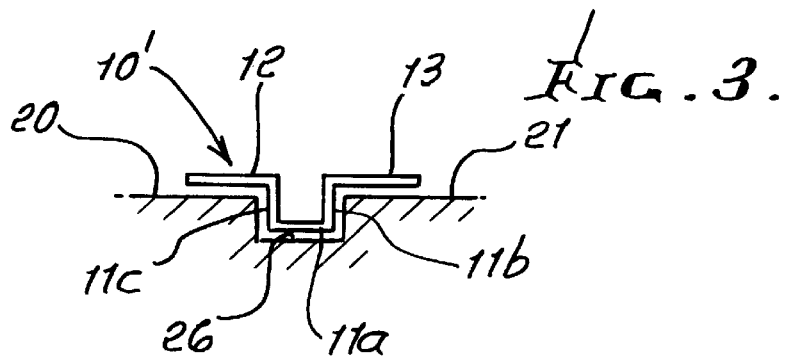
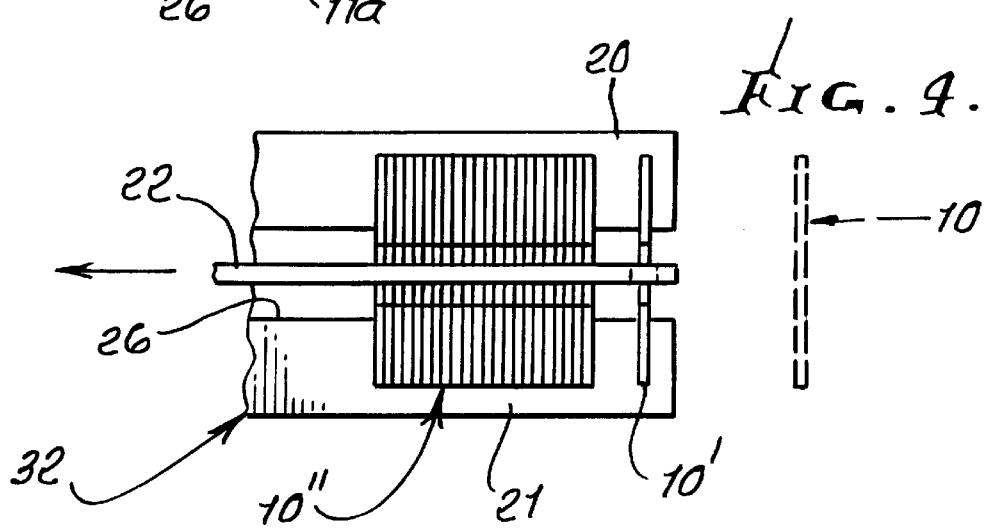

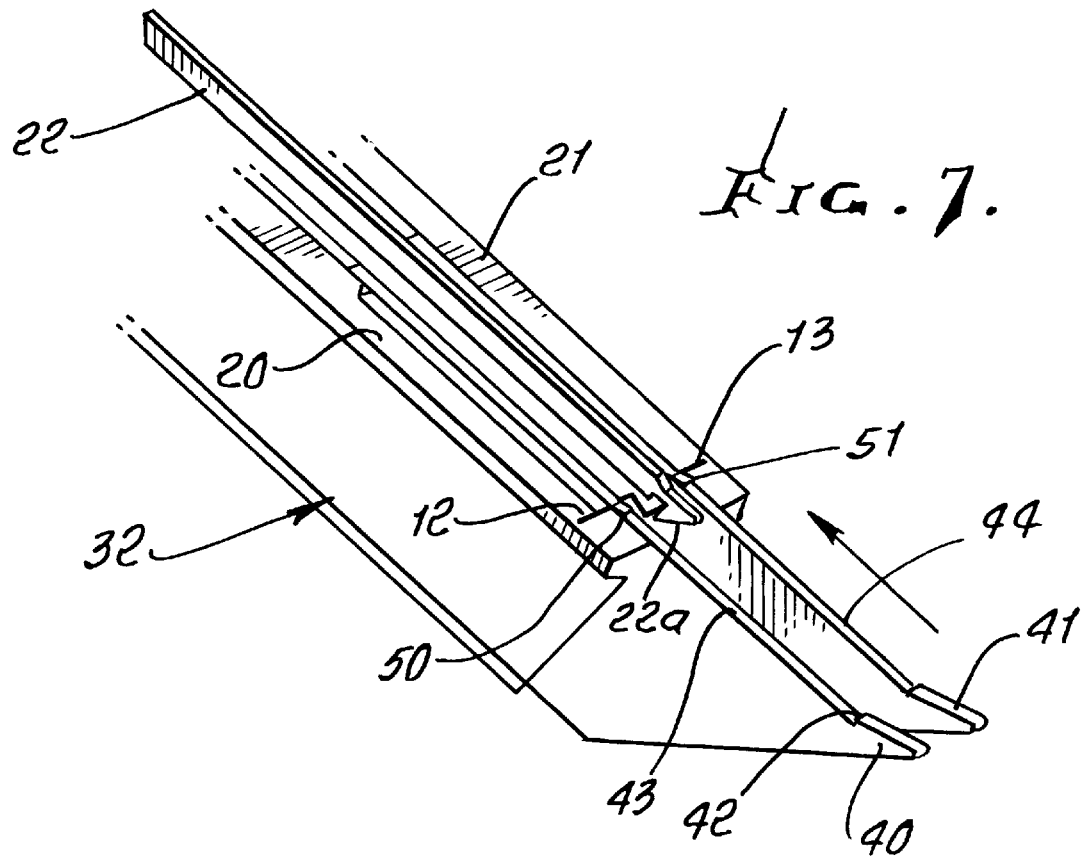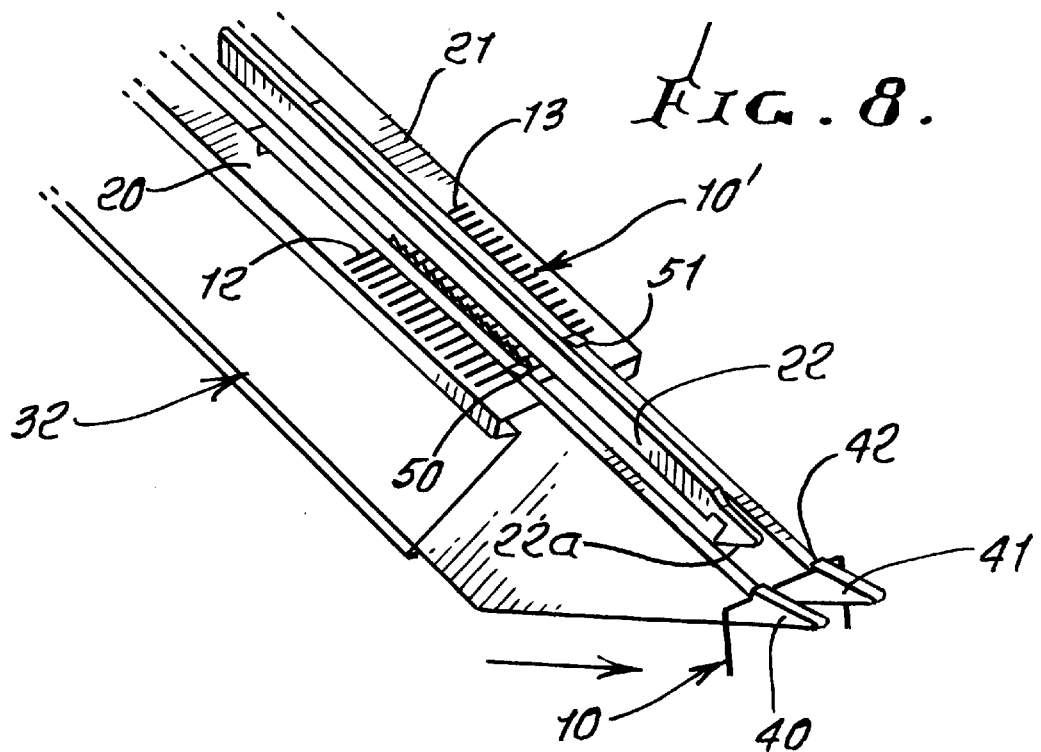

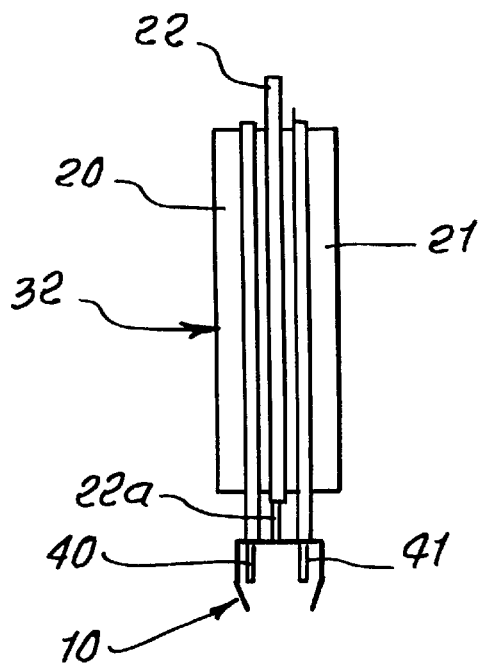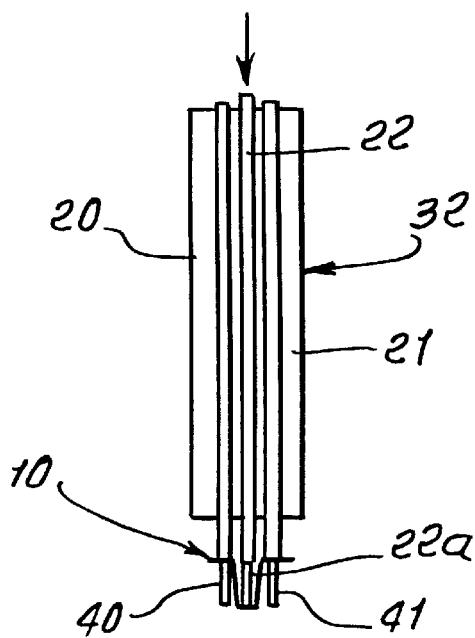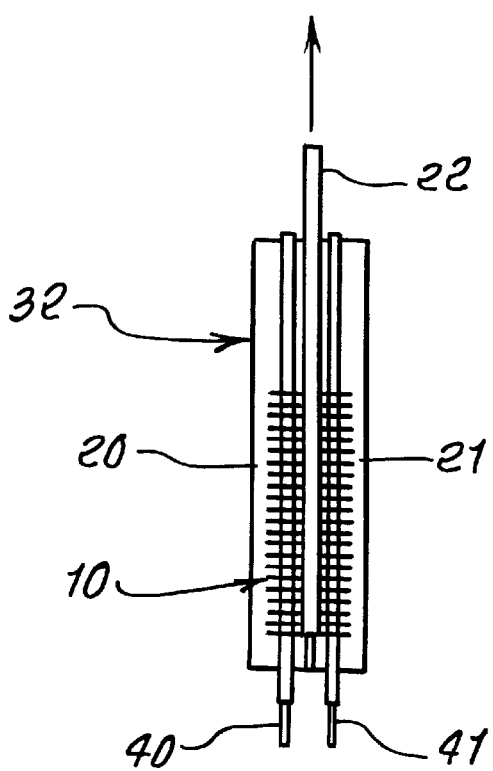

TISSUE STAPLE REMOVER

BACKGROUND OF THE INVENTION

This invention relates generally to removal of surgical staples from patients' tissue, and more particularly concerns apparatus and method to accomplish safer and less expensive staple removal.

Typically, instruments employed by physicians to remove surgical staples require two hands to manipulate and/or operate. One hand operates the staple remover and the other hand dispenses the staple with a towel. This procedure is risky because the contaminated staples are very sharp and often penetrate through the towel and the doctors rubber glove. There is great need for a safer and less expensive disposable tool to perform this procedure.

SUMMARY OF THE INVENTION

It is a major object of the invention to provide apparatus and method to meet the above need. Basically, the method concerns removing, deforming and storing of a staple having legs and a cross-piece, and includes the steps:

a) deforming the staple to cause the cross-piece to have a deformed medial portion, and displacing the legs to extend generally laterally and oppositely, b) and bodily displacing the staple in response to grasping of said deformed medial portion, to bring the legs into engagement with the support.

The method may be carried out by employing an elongated staple engaging tool having at least one cam surface, and manipulating the tool to cause the cam surface to engage the staple, and to deform the staple as will be seen. Deforming of the staple may typically and advantageously effect cross-piece deformation to itself have a U-shaped medial portion; and the legs may be deformed to extend in opposite directions away from the U-shaped medial portion. Accordingly, the staple is deformed to reduce the size of its U-shape.

Another object includes storing the then deformed staples sequentially, and in a row, on a platform.

Apparatus embodying the invention comprises:

a) multiple parts having operative interconnection, and relatively movable to retract a removed staple from a tissue zone, b) and a storage zone toward which removed staples are retracted for storage in response to relative movement of said parts, the storage zone carried by at least one of said parts.

As will be seen, the storage zone is typically a platform on which removed staples are stored, sequentially. Spring means may be used to retain retracted staples to the platform.

Another object is to provide one of the parts in the form of a plunger configured and projecting to bend the staple in response to plunger forward advancement, and to retract the bent staple for storage in said zone.

Yet another object is to provide two other of such parts to project at opposite sides of the plunger to hook under the staple prior to bending of the staple by the plunger forward end portion. A channel may be provided between said two other parts to receive a reduced size, deformed U-shaped medial portion of a staple cross-piece.

A further object is to provide parts which are operatively interconnected, and including two handles manipulable to effect relative movement of such parts.

These and other objects and advantages of the invention, as well as the details of an illustrative embodiment, will be more fully understood from the following specification and drawings, in which:

DRAWING DESCRIPTION

FIGS. 1–4 are views showing progressive deformation and storage of a surgical staple;

FIG. 7 is a view of the FIGS. 5 and 6 apparatus in a retracting and storing mode with respect to a staple deformed into FIG. 2 configuration;

FIG. 8 is a view of the FIGS. 5–7 apparatus in a staple storing mode, and the staple retractor returning to FIG. 5 mode;

FIGS. 9–11 are partial plan views of the apparatus as shown in FIGS. 5–7 modes, respectively.

DETAILED DESCRIPTION

Figure 5:
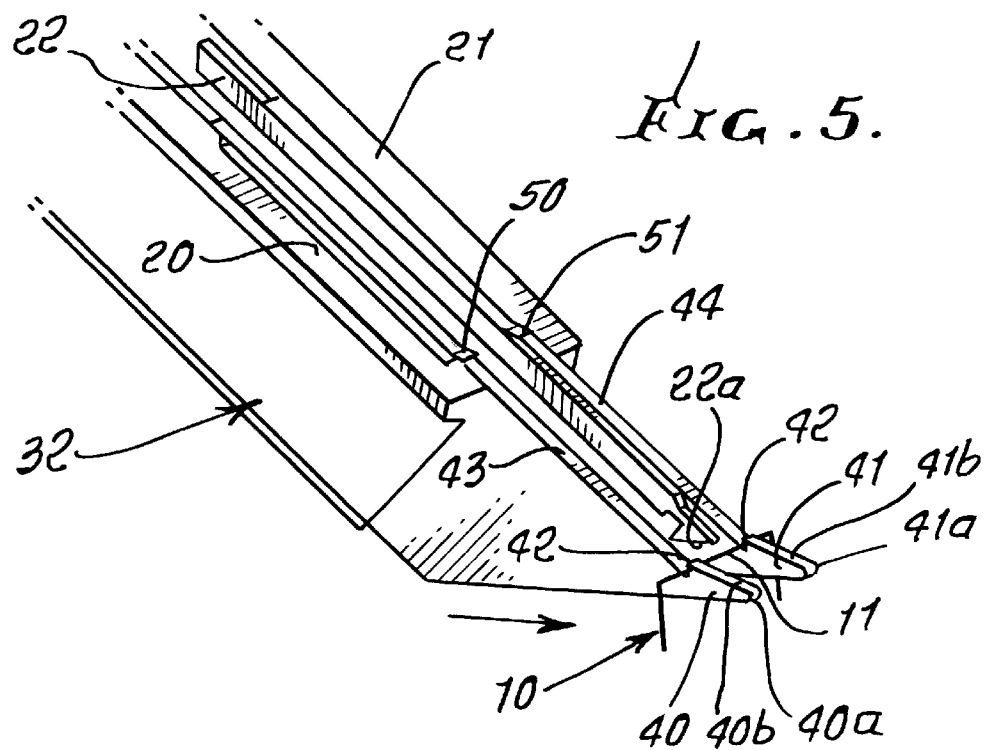
FIG. 5 is a perspective view of apparatus to engage and deform a staple in its FIG. 1 configuration.
Figure 6:
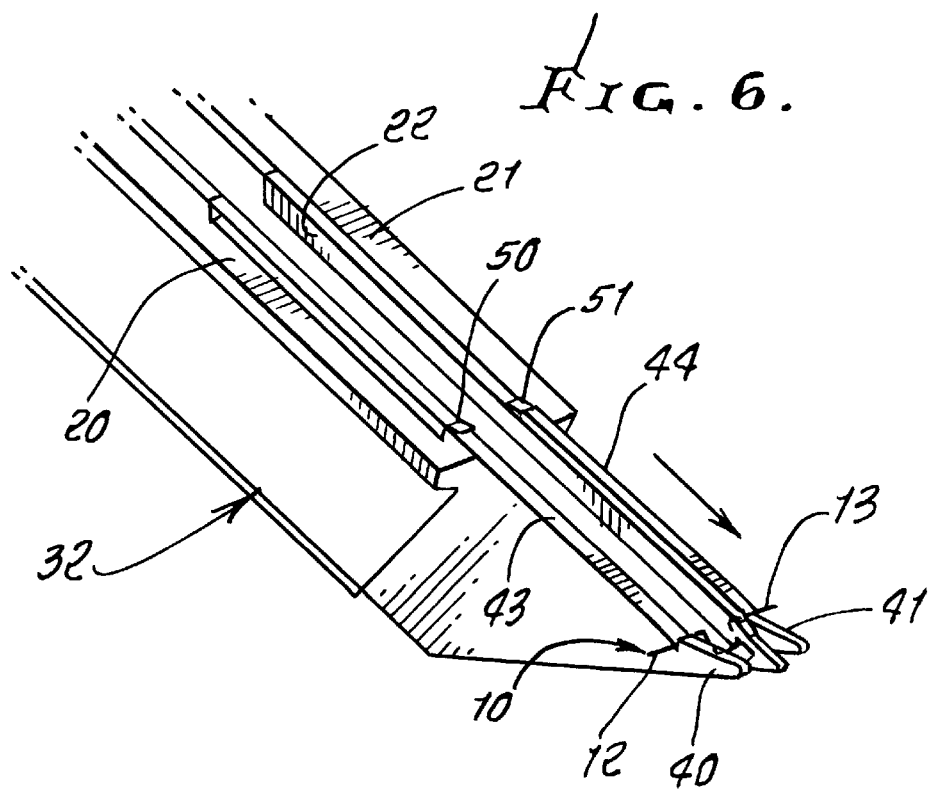
FIG. 6 is a view of the FIG. 5 apparatus having deformed a staple into a configuration as also seen in FIG. 2.

In FIG. 1, a surgical staple 10 has a cross-piece 11 projecting horizontally, and two legs 12 and 13 projecting generally downwardly, into body tissue 14. See also FIGS. 5 and 9, showing the U-shaped staple. In FIG. 2, the FIG. 1 staple 10 has been deformed, for example by the FIGS. 5 and 6 apparatus, the deformed staple also depicted in FIG. 6. Note that the FIG. 2 wire staple now has a smaller medial portion 15 of downward U-shape (as opposed to upward and larger U-shape seen in FIG. 1). The medial portion 15 was created by deforming the cross-piece 11, and resulting in a smaller cross-piece 11a and shorter legs 11b and 11c. Also, legs 12 and 13 have been deformed and displaced to extend generally horizontally laterally, and oppositely. Also, legs 12 and 13 are drawn closer together, in FIG. 2 (see spacing $S_2$) as compared with their spacing $S^1$ in FIG. 1. In FIG. 3 the FIG. 2 staple 10' is being displaced toward and onto a platform having spaced horizontal surfaces 20 and 21, to support legs 12 and 13.

See also FIG. 4, showing the staple 10' being displaced to the left, as by a retractor plunger 22, and on the platform. Its initial position is seen at 10 in FIG. 4. A sequence of staples 10" is shown in stored position on the platform surfaces 20 and 21. Note the channel 26 provided between the platform surfaces 20 and 21, and of a depth to receive the downwardly deformed, smaller U-shaped medial portions of the sequence of staples. See also FIGS. 5–8, and 9–11, in these regards. The instrument body 32 supports or carries the platforms and forms the channel 26. The instrument retractor plunger 22 is elongated over the elongated channel and moves endwise to engage, deform and retract the staples.

The instrument also has two elongated parts 40 and 41, with forward tips 40a and 41a having cam surfaces 40b and 41b to initially engage the underside of the staple cross-piece 11, as seen in FIG. 5, and to lift the staple as the cam surfaces are moved to the right, in FIG. 5. Cross-piece 11 then drops over shoulders 42, and onto elongated rails 43 and 44 provided by 40 and 41. See FIG. 5.

Subsequent rightward and downward movement of plunger 22 causes its cam surface 22a, facing downwardly, to downwardly deform the cross-piece 11 into FIG. 2 configuration; and at the same time the staple legs 12 and 13 are drawn over and bent by shoulders 42, into FIG. 2 configuration. See FIG. 6.

Thereafter, leftward and upward retraction of the plunger 22 causes shoulder 22a on the plunger to engage and retract the reduced cross-piece 11a (see FIG. 3), carrying the staple into storage position on the platform 20 and 21, as referred to above. See FIG. 7. Spring arms 50 and 51 extending over those platforms, press down on the legs 12 and 13 to hold the staples in stored position, as seen in FIG. 8 at 10'.

Figure 12:
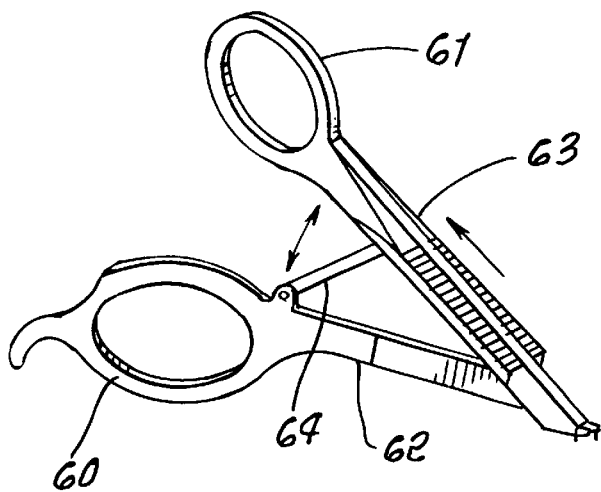
FIGS. 12–14 are perspective views of an instrument usable to relatively displace the parts of the device referred to in FIGS. 5–8.
Figure 13:
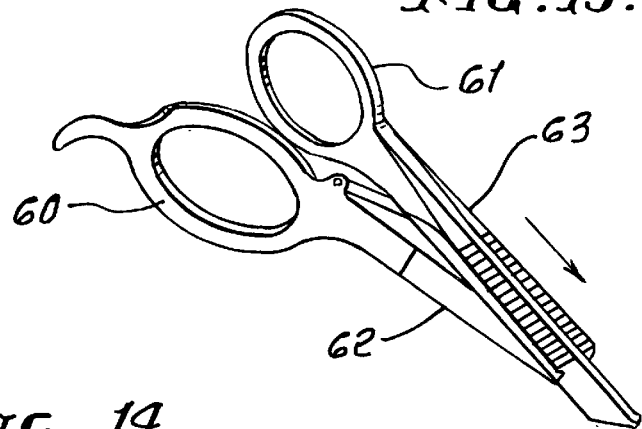
Figure 14:
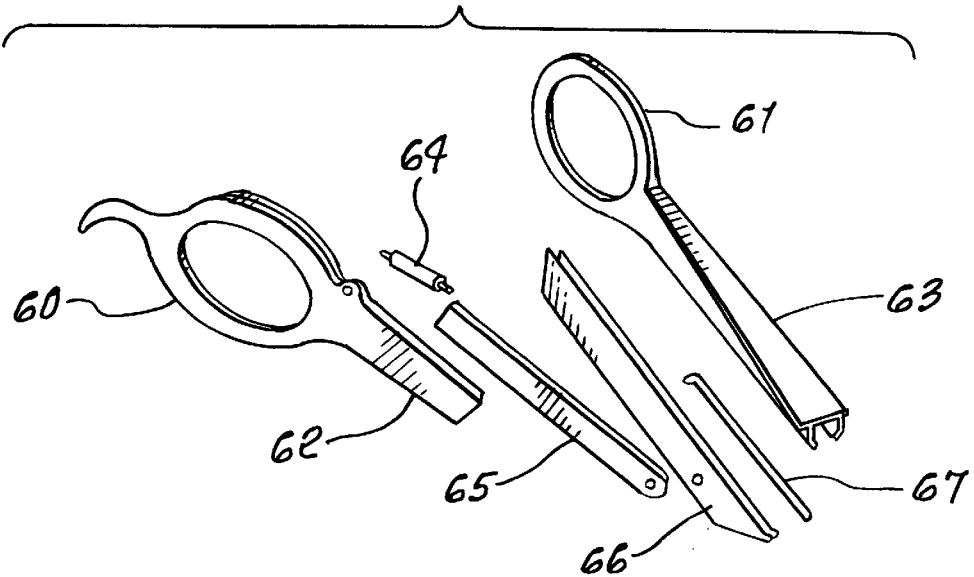

FIGS. 12–14 show instrument parts that relatively move to cause extension and retraction of the plunger. See scissors loops 60 and 61; scissor arms 62 and 63, and interconnecting elements 64–67. Arms 62 and 63 pivotally interconnect, and as 60 closes toward 61, rod 69 connected to the plunger advances forwardly to displace the plunger to FIG. 6 position. Relative separation of the loops retracts the plunger.

I claim:

1. In a surgical staple remover, a combination comprising
    a) multiple parts having operative interconnection, to retract a removed staple from a tissue zone,
    b) and a storage zone toward which removed staples are retracted for storage in response to relative movement of said parts, said storage zone carried by at least one of said parts,
    c) said storage zone being an elongated platform on which removed staples are stored, sequentially, and including said removed staples having deformed legs on the platform,
    d) and including at least one spring arm above said deformed legs on the platform to hold the removed staples in sequential position.

2. The combination of claim 1 wherein one of said parts is a plunger configured and projecting to deform the staple in response to plunger formed forward advancement, and to retract the deformed staple for storage in said zone.

3. The combination of claim 2 wherein the plunger has a forward end portion with an inclined surface engageable with the staple to bend the staple for deflecting staple legs into alignment.

4. The combination of claim 3 wherein two of said parts project at opposite sides of the plunger to hook under the staple prior to bending of the staple by said plunger forward end portion.

5. The combination of claim 4 wherein the plunger forward end portion has a sideward facing shoulder engageable with the bent staple to retract it in response to plunger retraction.

6. The combination of claim 1 wherein said parts are operatively interconnected, and include two handles manipulable to effect part movement.

7. The combination of claim 4 including a channel between said two other parts to receive a reduced size, deformed U-shaped medial portion of a staple cross-piece.

8. In a staple removing, deforming and storage process, the staple having legs and a lateral cross-piece, the steps that include
    a) deforming the staple to cause the cross-piece to have a deformed medial portion, and displacing the legs to extend generally laterally and oppositely,
    b) providing an elongated platform to receive a succession of removed staples,
    c) bodily displacing the staple in response to grasping of said deformed medial portion, to bring said legs into engagement with the platform,
    d) and providing spring arm means directly above the platform and receiving legs of removed staples between said spring arm means and said platform.

9. The method of claim 8 including providing an elongated staple engaging tool having at least one cam surface, and manipulating said tool to cause said cam surface to engage the staple, and to deform the staple as per step a) of claim 10.

10. The method of claim 9 wherein said deforming of the staple causes said cross-piece to have a U-shaped medial portion.

11. The method of claim 8 wherein said deforming of the staple also causes said cross-piece to have reduced length portions extending in alignment with said displaced legs.

12. In a staple removing process, wherein the staple has a U-shape, with a long cross-piece, and legs extending in generally the same direction, the steps that include
    i) deforming the staple to have a reduced length U-shape,
    ii) said deforming causing the resultant staple to have a short cross-piece and legs extending in generally opposite directions,
    iii) and sequentially storing the deformed staples in a row, on a platform, and providing elongated spring arm means directly above the platform to retain a succession of deformed staples in said row.

13. The method of claim 12 including providing a channel adjacent the platform to receive deformed medial portions of the cross-pieces of staples sequentially stored at said platform.

* * * * *